United States Patent
Fisher et al.

(10) Patent No.: US 7,189,239 B2
(45) Date of Patent: Mar. 13, 2007

(54) SAW BLADE HAVING A PREARRANGED HUB SECTION

(75) Inventors: Michael G. Fisher, El Dorado Hills, CA (US); Kevin Cordes, Placerville, CA (US)

(73) Assignee: Synvasive Technology, Inc. a California corporation, El Dorado Hills, CA (US)

( * ) Notice: Subject to any disclaimer, the term of this patent is extended or adjusted under 35 U.S.C. 154(b) by 31 days.

(21) Appl. No.: 10/356,213

(22) Filed: Jan. 30, 2003

(65) Prior Publication Data

US 2004/0138668 A1 Jul. 15, 2004

Related U.S. Application Data

(60) Provisional application No. 60/440,113, filed on Jan. 14, 2003.

(51) Int. Cl.
*A61B 17/00* (2006.01)
*A61B 17/14* (2006.01)

(52) U.S. Cl. .................................... 606/82; 606/176

(58) Field of Classification Search .............. 606/82, 606/79, 176; D24/146; 30/519
See application file for complete search history.

(56) References Cited

U.S. PATENT DOCUMENTS

| | | | |
|---|---|---|---|
| 3,905,374 A | 9/1975 | Winter | 128/317 |
| 3,943,934 A | 3/1976 | Bent | 606/178 |
| 4,106,181 A | 8/1978 | Mattchen | 29/450 R |
| 4,386,609 A | 6/1983 | Mongeon | 606/53 |
| 4,461,296 A | 7/1984 | Hodge | 606/176 |
| 4,513,742 A | 4/1985 | Arnegger | 606/178 |
| 4,584,999 A | 4/1986 | Arnegger | 606/178 |
| 4,617,930 A | 10/1986 | Saunders | 606/82 |
| 4,637,391 A | 1/1987 | Schlein | 606/172 |
| 4,872,452 A | 10/1989 | Alexson | 606/85 |
| 5,002,555 A | 3/1991 | Petersen | 606/176 |
| 5,122,142 A | 6/1992 | Pascaloff | 606/82 |
| 5,178,626 A | 1/1993 | Pappas | 606/178 |
| D337,160 S | 7/1993 | Evans | D24/146 |
| 5,263,972 A | 11/1993 | Evans et al. | 606/176 |
| 5,265,343 A | 11/1993 | Pascaloff | 30/335 |
| D343,247 S | 1/1994 | Walen | D24/146 |
| 5,306,285 A | 4/1994 | Miller et al. | 606/177 |
| D351,907 S | 10/1994 | Matthai et al. | D24/146 |

(Continued)

*Primary Examiner*—Pedro Philogene
(74) *Attorney, Agent, or Firm*—Daniel J. Meaney, Jr.

(57) ABSTRACT

A saw blade comprising a blade body having a longitudinal axis, a cutting means disposed at a first end of the blade body and a prearranged hub section having an outer periphery located at a second end of the blade body is shown. The prearranged hub section comprises an elongated slot formed in the hub section which extends from the outer periphery along a longitudinal axis to a U-shaped cut-out forming a hub center. The hub center is located along the longitudinal axis. The hub section includes a plurality of slots, each of the slots having a generally rectangular elongated blade driving enabling section having one end which terminates in an expanded bulbous blade driving disabling section in a position opposed to the hub center. The respective generally rectangular elongated blade driving enabling section are disposed in a pattern along a radius centered at the hub center. The respective generally rectangular elongated blade driving enabling section of each slot being configured for engaging a selected blade driving structure and for disengaging from a different blade driving member.

16 Claims, 4 Drawing Sheets

U.S. PATENT DOCUMENTS

| | | | |
|---|---|---|---|
| 5,382,249 A | 1/1995 | Fletcher | 606/176 |
| D362,065 S * | 9/1995 | Goris | D24/146 |
| 5,489,285 A * | 2/1996 | Goris | 606/82 |
| 5,496,316 A * | 3/1996 | Goris | 606/82 |
| 5,507,763 A | 4/1996 | Peterson et al. | 606/176 |
| 5,694,643 A | 12/1997 | Fujiwara | 30/166.3 |
| 5,694,693 A * | 12/1997 | Hutchins et al. | 30/166.3 |
| D394,315 S | 5/1998 | Fisher | D24/146 |

* cited by examiner

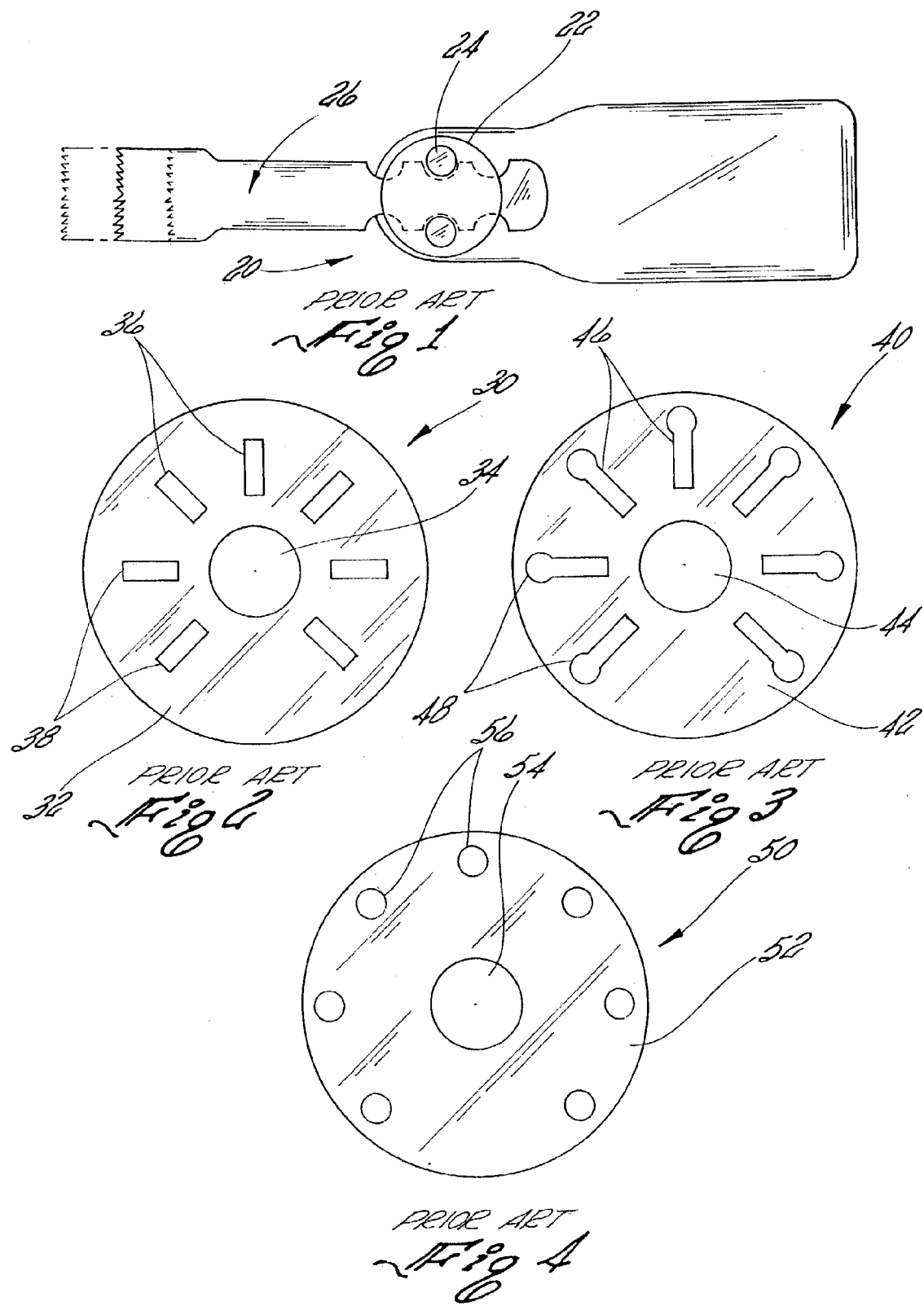

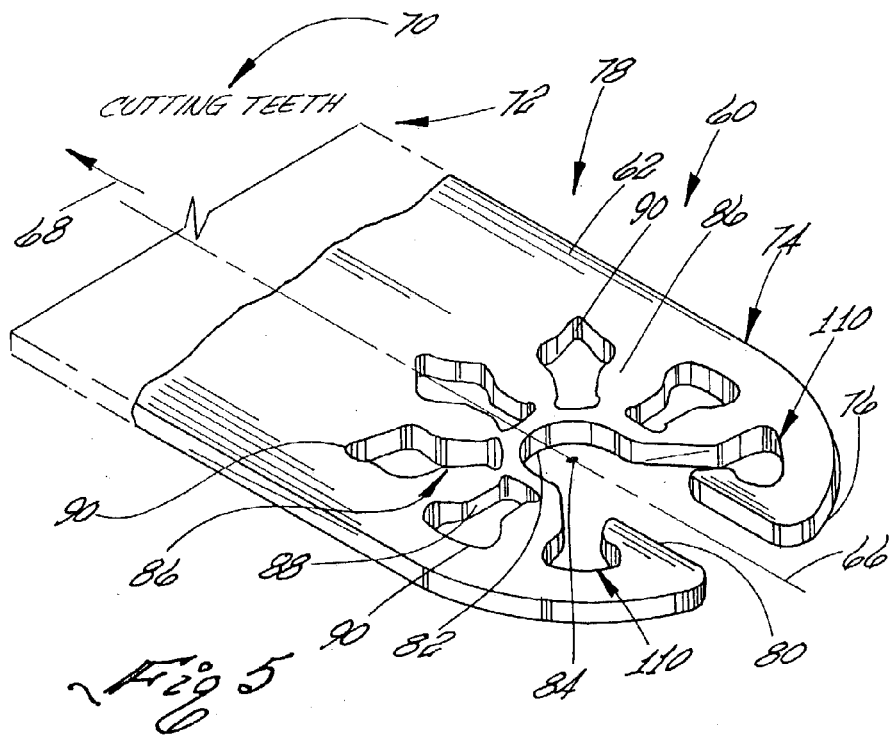
Fig 5
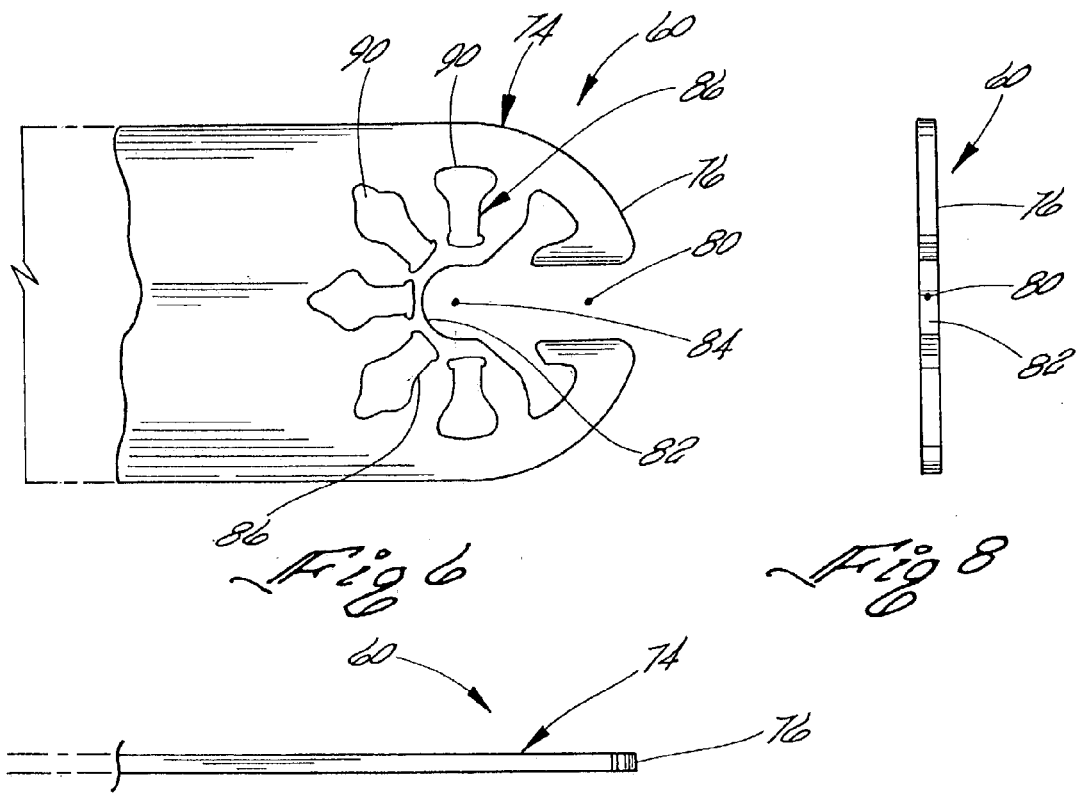
Fig 6
Fig 8
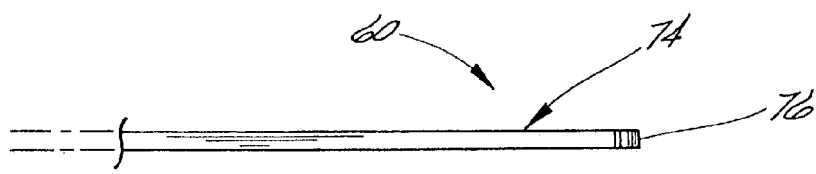
Fig 7

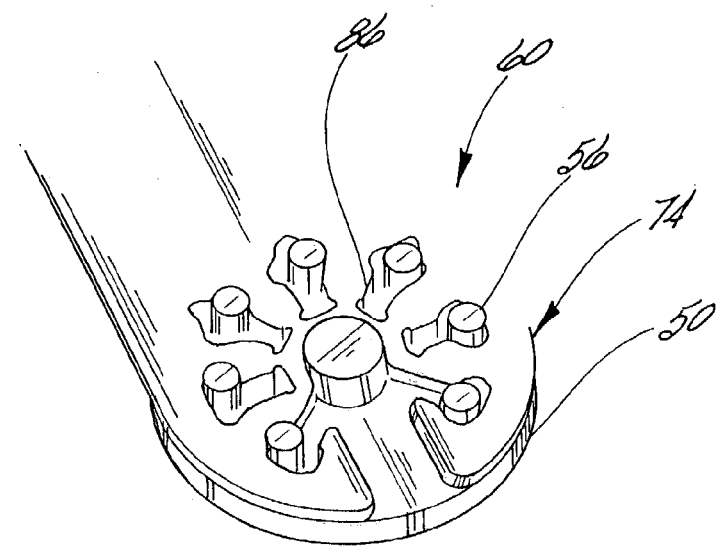
Fig 11
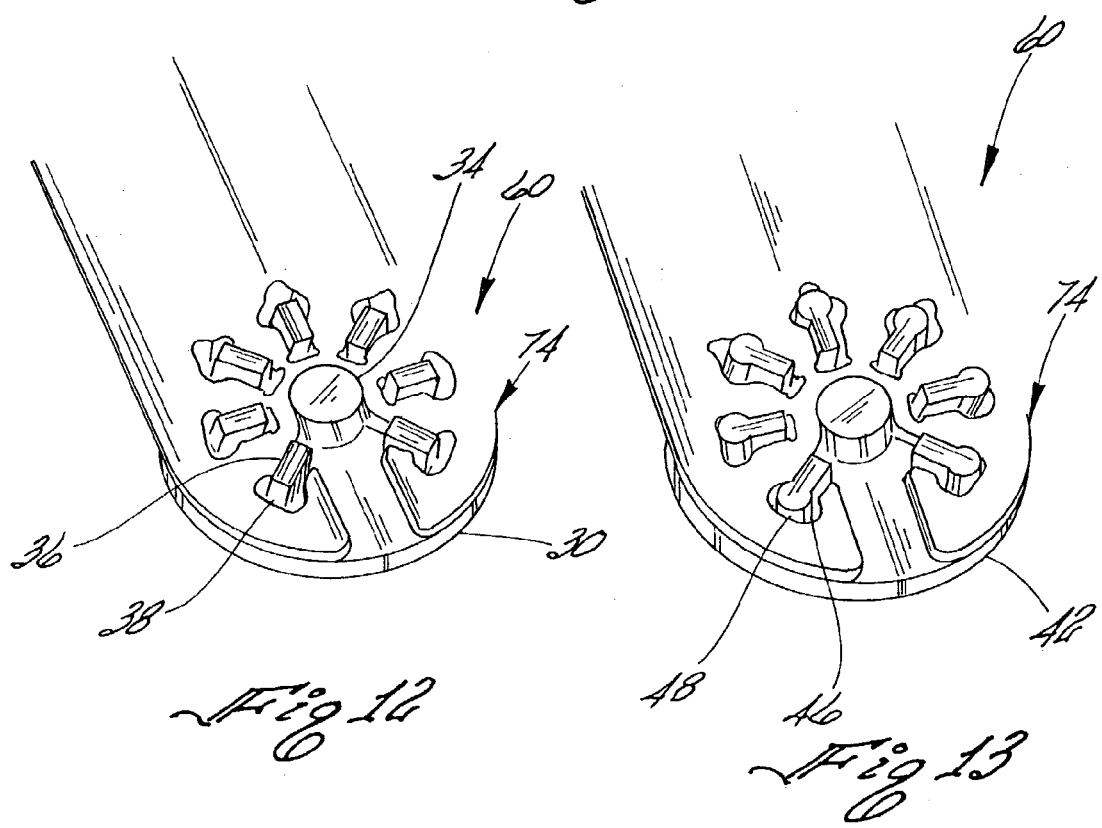
Fig 12
Fig 13

SAW BLADE HAVING A PREARRANGED HUB SECTION

CROSS-REFERENCES TO RELATED APPLICATIONS

This Application claims the benefit, under Title 35, United States Code §119(e), of U.S. Provisional patent application Ser. No. 60/440,113 filed Jan. 14, 2003 and entitled SAW BLADE HAVING A PREARRANGED HUB SECTION.

STATEMENT REGARDING FEDERALLY SPONSORED RESEARCH OR DEVELOPMENT

Not Applicable

REFERENCE TO A "MICROFICHE APPENDIX" (SEE 37 CFR 1.96)

Not Applicable

BACKGROUND OF THE INVENTION

1. Field of the Invention

The present invention relates to a power driven surgical saw blade and more particularly relates to a surgical saw blade having a prearranged hub section which is configured to be driven in an oscillating manner by a pneumatic or electrically powered actuator having a clamp for removeably mounting the blade. The prearranged hub section includes slots having generally rectangular elongated blade driving enabling sections each of which terminate in unexpanded bulbous blade driving disabling section which is configured for disengaging from a plurality of driving circular pins arranged in a pattern by deflecting a driving force therefrom along a locus of points which avoids driving the surgical saw blade in response to a driving force therefrom.

2. Description of the Prior Art

Powered saws are frequently used for surgical procedures including orthopedic surgery, and other operations requiring removal of bone material. A surgical saw blade, the blade clamp, and blade drive must be compatible to effective use the same. Typically, the saw blade has a low blade weight to minimize oscillating mass and the hub section is configured to enable a secure mounting or clamping of the surgical saw blade to a selected saw blade driver. The hub section is configured to enable a saw blade to be used with a designated number of saw blade drivers. It is known in the art to refer to such saw blades as universal saw blades.

The prior art includes a variety of cooperating blades, clamps and oscillating drive mechanisms which are configured to be used with a surgical saw blade having a specially configured hub section.

U.S. Pat. No. 5,265,343 discloses a blade and a corresponding clamp mechanism which provides, by the circular arrangement of round driving pins and clamping faces, a secure mount for the blade by way of the cooperating holes in the hub section of the surgical saw blade. One set of blades for use in a clamp such as described in U.S. Pat. No. 5,265,343 is shown as FIGS. 5A through 5C in U.S. Pat. No. 5,306,285. Another blade, for use in a clamp similar to the clamp described in U.S. Pat. No. 5,265,343 is shown in FIG. 6A of U.S. Pat. No. 5,306,285.

Another clamp mechanism and associated blade hub is shown in U.S. Pat. Nos. 5,496,316 and 5,489,285. The clamp described in the in U.S. Pat. Nos. 5,496,316 and 5,489,285 is similar in function to the clamp described in U.S. Pat. No. 5,265,343 except that the clamp described in the in U.S. Pat. Nos. 5,496,316 and 5,489,285 use rectangular driving lugs instead of round driving pins.

The rectangular driving lugs shown in U.S. Pat. Nos. 5,496,316 and 5,489,285 and the round driving pins shown in U.S. Pat. No. 5,265,343 are both arranged in a circular pattern and both have clamping faces. The clamps described in U.S. Pat. No. 5,265,343 and U.S. Pat. No. 5,496,316 both have means for biasing the blade against one clamping face.

Another related prior art saw blade configured for use with a rectangular lug clamp, such as that shown in the U.S. Pat. No. 5,496,316 is shown in U.S. Design Pat. DES 343,247. The blade hub shown in the U.S. Design Pat. DES 343,247 has radial slots formed to fit lugs, such as the lugs shown in U.S. Pat. No. 5,496,316. The radial slots shown in U.S. Design Pat. DES 343,247 are closed at both ends. This is different in form than the slot shown in U.S. Pat. No. 5,496,316 that are open to and communicate with the primary U-shaped slot.

It is known in the art that the LINVATEC-HALL VERSIPOWER.RTM.PLUS OSCILLATOR has a clamp substantially identical in structure, function, and operation as the clamp shown in U.S. Pat. No. 5,496,316.

It is also known in the art that the LINVATEC-HALL SERIES 3.TM. and LINVATEC-HALL SERIES 4.TM. device contain a clamp substantially identical in structure and function to clamp described in U.S. Pat. No. 5,265,343.

The MicroAire.RTM. Powermaster.TM. 7200 Oscillating Saw contains a clamp which mounts blades interchangeably with saw blades shown in clamps described in U.S. Pat. No. 5,694,693.

For proper operation using clamps of the form shown in U.S. Pat. No. 5,265,343, the round holes formed in the blade hub must precisely fit and cooperate with the round locking driving pins of the saw blade driver. The reason is that radial motion to the saw blade is imparted through the driving pins and any clearance between the blade holes and the round pins will allow motion or relative movement of the pins within the hub holes. As mismatch may result in erratic blade motion, accelerated wear on the round driving pins and possible fatigue-related failure in the blade hub.

Likewise, the lugs of the clamp shown in U.S. Pat. No. 5,496,316 must fit snug against the radial slots of the blade. Accordingly, a saw blade hub formed to fit the round driving pins of the clamp shown in U.S. Pat. No. 5,265,343 will not have the elongated slots required for the rectangular lugs of the clamp shown in U.S. Pat. No. 5,496,316. Further, a saw blade having slots formed and dimensioned such for use in the clamp shown in U.S. Pat. No. 5,496,316 will not fit properly with the round driving pins shown in the clamp shown in U.S. Pat. No. 5,265,343 unless the rectangular lugs have the same width as the diameter of the round pins.

U.S. Pat. No. 5,694,693 discloses a universal saw blade hub that is configured to be operative with the clamps shown in U.S. Pat. Nos. 5,496,316 and 5,265,343.

Further the saw blade shown in FIG. 5 of U.S. Pat. No. 5,496,316 appears to be able to fit either a round driving pin clamp shown in U.S. Pat. No. 5,265,343 or rectangular lug clamp shown in U.S. Pat. No. 5,496,316. The saw blade shown in FIG. 5 of U.S. Pat. No. 5,496,316 appears to achieve this objective by having enlarged circular openings at the outer end of each of the slots wherein the holes having a wider diameter than the width of the slot.

It is also known in the art that a saw blade driving clamp may have rectangular driving lugs which terminate in a substantially circular outer ends. One example of such a blade is shown in U.S. Pat. No. 5,496,316.

Under certain circumstances, it may be desirable design and fabricate a saw blade which is configured to be driven only by certain selected saw blade drivers and to not be driveable by another saw blade driver. None of the saw blades drivers or saw blades known in the art anticipate, disclose, suggest or teach a prearranged hub section which is configured to have slots which can be engaged and driven by a rectangular lugs terminating in a substantially rectangular outer end arranged in a pattern or a plurality of driving rectangular lugs terminating in a substantially circular outer end arranged in a pattern to drive the saw blade and wherein each slot has an expanded bulbous blade driving disabling section configured to prevent being driven by a plurality of driving circular pins arranged in a pattern.

BRIEF SUMMARY OF THE INVENTION

The present invention discloses and teaches a new, novel and unique saw blade comprising a blade body having a longitudinal axis, a cutting means disposed at a first end of the blade body and a prearranged hub section having an outer periphery located at a second end of the blade body. The prearranged hub section comprises an elongated slot formed in the hub section which extends from its outer periphery along a longitudinal axis to a U-shaped cut-out forming a hub center wherein the hub center is located along the longitudinal axis. The prearranged hub section includes a plurality of slots. Each of the slots have a generally rectangular elongated blade driving enabling section having one end which terminates in an expanded bulbous blade driving disabling section in a position opposed to the hub center. The respective generally rectangular elongated blade driving enabling section are disposed in a pattern along a radius centered at the hub center. The respective generally rectangular elongated blade driving enabling section of each slot are configured for engaging with at least one of a plurality of driving rectangular driving lugs terminating in a substantially rectangular outer end arranged in a pattern and a plurality of driving rectangular driving lugs terminating in a substantially circular outer end arranged in a pattern to drive the saw blade in response to a driving force therefrom. The respective expanded bulbous blade driving disabling section of each slot is configured for disengaging from a plurality of driving circular pins arranged in a pattern by deflecting a driving force therefrom along a locus of points which avoids driving the surgical saw blade in response to a driving force therefrom.

Therefore, one advantage of the present invention is that a surgical saw blade can be configured to be driven only by a saw blade driving clamp having either a plurality of rectangular driving lugs terminating in a substantially rectangular outer end arranged in a pattern or a plurality of rectangular driving lugs terminating in a substantially circular outer end arranged in a pattern to drive the saw blade in response to a driving force therefrom.

Another advantage of the present invention is that the respective expanded bulbous blade driving disabling section of each slot is configured to prevent the saw blade from being driven by a saw blade driving clamp having circular driving pins arranged in a pattern.

Another advantage of the present invention is that the prearranged saw blade hub section expanded bulbous blade driving disabling section of each slot is configured to deflect a driving force therefrom along a locus of points which avoids driving the saw blade in response to a driving force a saw blade driving clamp having circular lugs arranged in a pattern.

Another advantage of the present invention is that a surgical saw blade using the teachings of the present invention can be used for penetrating bone when the surgical saw blade is operatively coupled to an oscillatory power tool.

Another advantage of the present invention is that a surgical saw blade using the teachings of the present can be used in a method of cutting bone.

BRIEF DESCRIPTION OF THE DRAWING

The present invention will become more fully understood from the following detailed description of a preferred but non limiting embodiment thereof, described in connection with the accompanying drawings, wherein:

FIG. 1 is a top view of a prior art combination surgical saw and cutting blade wherein the blade retention device comprises a pair of parallel pins for clamping and driving a surgical saw blade;

FIG. 2 is a diagrammatic representation of a prior art plurality of rectangular driving lugs formed in a predetermined pattern wherein the ends of the rectangular driving lugs are square shaped for clamping and driving a surgical saw blade;

FIG. 3 is a diagrammatic representation of a prior art plurality of rectangular driving lugs formed in a predetermined pattern wherein the ends of the rectangular driving lugs are circular shaped for clamping and driving a surgical saw blade;

FIG. 4 is a diagrammatic representation of a prior art plurality of circular shaped driving pins formed in a predetermined pattern for driving a saw blade having a hub portion defining circular shaped openings to precisely fit and be driven by the circular shaped driving pins;

FIG. 5 is a top front and left side perspective view of a surgical saw blade having a prearranged hub section incorporating the teachings of the present invention;

FIG. 6 is a top plan view of the surgical saw blade of FIG. 5;

FIG. 7 is a front elevational view of the surgical saw blade of FIG. 6;

FIG. 8 is a right end elevational view of the surgical saw blade of FIG. 6;

FIG. 11 is a pictorial representation of a combination of the saw blade driver having a plurality of circular shaped driving pins and the surgical saw blade of the present invention having a prearranged hub section for disabling driving of the surgical saw blade by the oscillatory driving motion of the circular shaped driving pins shown in FIG. 9 with the circular shaped driving pins shown at a plus five degree position;

FIG. 12 is a pictorial representation of a combination of the saw blade driver having a plurality of rectangular shaped driving lugs terminating in a substantially rectangular outer end arranged in a pattern for enabling driving of a surgical saw blade of the present invention illustrating that the generally rectangular elongated blade driving enabling section of each slot is configured for engaging with at least one of a plurality of rectangular driving lugs terminating in a substantially rectangular outer end and being responsive to the oscillatory driving motion of the rectangular shaped driving lugs to drive the surgical saw blade; and FIG. 13 is a pictorial representation of a combination of the saw blade driver having a plurality of rectangular shaped driving lugs terminating in a substantially circular outer end arranged in a pattern for enabling driving of a surgical saw blade of the present invention illustrating that the generally rectangular elongated blade driving enabling section of each slot is configured for engaging with at least one of a plurality of rectangular driving lugs terminating in a substantially rectangular outer end and being responsive to the oscillatory driving motion of the rectangular shaped driving lugs to drive the surgical saw blade.

DETAILED DESCRIPTION OF THE INVENTION

Background

Figure 9:
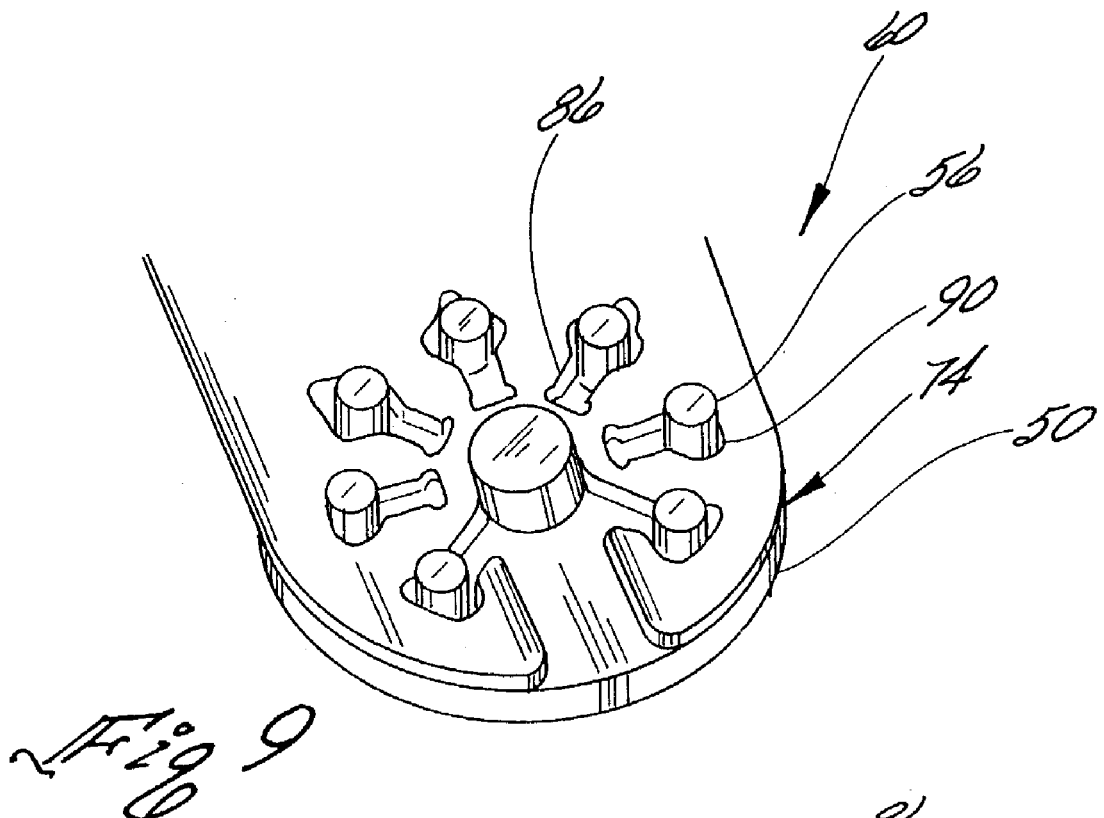
FIG. 9 is a pictorial representation of a combination of the saw blade driver having a plurality of circular shaped driving pins and a surgical saw blade of the present invention having a prearranged hub section for disabling driving of the surgical saw blade by the oscillatory driving motion of the circular shaped driving pins illustrating that expanded bulbous blade driving disabling section of each slot is configured for deflecting a driving force from the plurality of circular shaped driving pins along a locus of points which avoids driving of the surgical saw blade in response to a driving force from a plurality of circular shaped pins with the circular shaped driving pins shown at a zero degree position.

Due to the wide variety of surgical saw blade drivers available for use in the medical surgical field, surgical saw blade manufacturers attempt to design surgical saw blade drivers to be used with a proprietary surgical saw blade produced by that manufacturer. However, as each proprietary saw blade driver is developed, the manufacturers of surgical saw blades are sufficiently entrepreneurial to developed surgical saw blades having hub sections configured for being mounted onto and driven by one or more proprietary saw blade drivers. Several of the known prior art surgical saw blade drivers are discussed hereinbelow.

In FIG. 1, one known prior art combination surgical saw and cutting blade, generally shown by arrow 20, has a blade retention device 22 comprising a pair of parallel driving pins 24 for clamping and driving a surgical saw blade 26. The surgical saw blade is typical of the type offered for sale and sold by Synvasive Technology, Inc.

In FIG. 2, another known prior art surgical saw blade driver, shown generally by arrow 30, has a hub 32 having a central hub 34. The hub 32 has a plurality of rectangular shaped driving lugs 36 each of which terminate in a substantially rectangular outer end 38 formed in a predetermined pattern therearound for clamping and driving a surgical saw blade. The saw blade driver is typical of the type offered for sale and sold by Linvatec-Hall Surgical Corporation under the Trademark VERSIPOWER PLUS.

In FIG. 3, another known prior art surgical saw blade driver, shown generally by arrow 40, has a hub 42 having a central hub 44. The hub 42 has a plurality of rectangular shaped driving lugs 46 each of which terminate in a substantially circular outer end 48 formed in a predetermined pattern therearound for clamping and driving a surgical saw blade. The saw blade driver is typical of the type offered for sale and sold by Linvatec-Hall Surgical Corporation under the Trademark POWERPRO.

In FIG. 4., another known prior art surgical saw blade driver, shown generally by arrow 50, has a hub 52 having a central hub 54. Hub 52 has a plurality of circular shaped driving pins 56 formed in a predetermined pattern for driving a surgical saw blade. Typically, the surgical saw bald has a hub portion defining circular shaped openings disposed in a patterns to precisely fit and be driven by the circular shaped driving pins 56. The saw blade driver is typical of the type offered for sale and sold by Linvatec-Hall Surgical Corporation under the Trademark VERSIPOWER.

Several surgical saw blade manufacturers have elected to design and sell a universal surgical saw blade that has a hub section configured to be driven by one or more of the known surgical saw blade drivers. This is discussed above in the Description of the Prior Art.

For a number of reasons, a surgical saw blade manufacturer may elect to design and sell a surgical saw blade that has a hub section configured as a prearranged hub section to be enabled to be driven by one or more of the known surgical saw blade drivers and to be disabled to prevent being driven by at least one of the known surgical saw drivers.

The surgical saw blade having a prearranged hub section of the present invention represents a new, novel and unique approach for the design, fabrication, sale and use of a surgical saw blades for specific use with specific surgical saw blade drivers.

Description of Surgical Saw Blade Having a Prearranged Hub Section

The top front and left side perspective view of FIG. 5 and the views shown in FIGS. 6 through 8, illustrate the surgical saw blade having a prearranged hub section incorporating the teachings of the present invention and the surgical saw blade is shown generally by arrow 60.

In FIGS. 5 through 8, the surgical saw blade 60 comprises a blade body 62 having a longitudinal axis shown generally by dashed line 66. A cutting means depicted by arrow 68 and cutting teeth 70 is disposed at a first end or distal end 72 of the blade body 62. A prearranged hub section shown generally 74 has an outer periphery 76 located at a second end of proximal end 78 of the blade body 62.

The prearranged hub section 74 comprises an elongated slot 80 formed in the hub section 74 which extends from the outer periphery 76, along the longitudinal axis 66 to a U-shaped cut-out 82 forming a hub center 84. The hub center 84 is along the longitudinal axis 66.

The hub section 74 includes a plurality of slots 86. Each of the slots 86 have a generally rectangular elongated blade driving enabling section 88 having one end which terminates in an expanded bulbous blade driving disabling section 90 in a position opposed to or opposite to the hub center 84.

The respective generally rectangular elongated blade driving enabling section 88 is disposed in a pattern along a radius centered at the hub center 84.

The respective generally rectangular elongated blade driving enabling section 88 of each slot 86 is configured for engaging with at least one of a plurality of rectangular driving lugs terminating in a substantially rectangular outer end arranged in a pattern, such as the saw blade driver illustrated in FIG. 2, and a plurality of rectangular driving lugs terminating in a substantially circular outer end arranged in a pattern, such as the saw blade driver illustrated in FIG. 3.

Also, the respective expanded bulbous blade driving disabling section 90 of each slot 86 is configured for disengaging from a plurality of circular driving pins arranged in a pattern, such as the saw blade driver illustrated in FIG. 4.

FIGS. 5 and 6 show the specific structure of the expanded bulbous blade disabling section in the following manner. Two slots 110 are located one on each side of the elongated slot 84 and the expanded bulbous blade disabling section is substantially oval shape. Two slots 90 located one on each side of the hub center 88 have expanded bulbous blade disabling sections that are substantially oval shape similar to slots 110. Three slots 90 located around the periphery of the hub section 84 have expanded bulbous blade disability sections which are substantially oval shaped similar to slots 110 and 90, but further include an indentation extending substantially perpendicular to the substantially oval shape and in a direction away from the hub center 84. The substantially oval shape and indentation are dimensioned, shaped or otherwise fabricated for receiving in a non-contacting or non-engaging manner the circular shaped driving pins 56 as described below in connection with the description of FIGS. 9, 10 and 11 hereinbelow.

Figure 10:
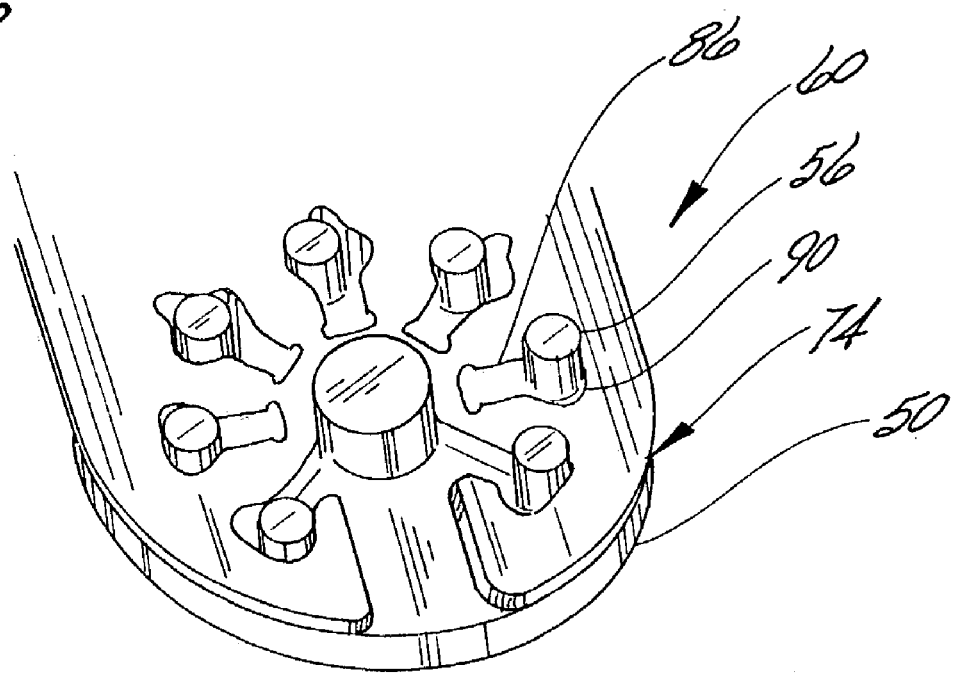
FIG. 10 is a pictorial representation of a combination of the saw blade driver having a plurality of circular shaped driving pins and the surgical saw blade of the present invention having a prearranged hub section for disabling driving of the surgical saw blade by the oscillatory driving motion of the circular shaped driving pins shown in FIG. 9 with the circular shaped driving pins shown at a minus five degree position.

FIGS. 9, 10 and 11 pictorially illustrate a combination of the saw blade driver 50 having a plurality of circular shaped driving pins 56 of FIG. 4 and a surgical saw blade 60 of the present invention having a prearranged hub section 74 for disabling driving of the surgical saw blade 60 by the oscillatory driving motion of the circular shaped driving pins 56. In FIG. 9, expanded bulbous blade driving disabling section 90 of each slot 86 is configured for receiving, in a non-contacting or non-engaging manner, the circular shaped driving pins 56 with the circular shaped driving pins shown at a zero degree position.

In FIGS. 10 and 11, the expanded bulbous blade driving disabling section 90 of each slot 86 is configured for deflecting a driving force from the plurality of circular shaped driving pins 56 along a locus of points which avoids driving of the surgical saw blade 60 in response to the driving force from a plurality of circular shaped pins 56. In FIG. 10, the circular shaped driving pins shown at a minus zero degree position. In FIG. 11, the circular shaped driving pins 56 are shown at a plus five degree position. This is the maximum driving pattern of the circular shaped driving pins and the expanded bulbous sections 90 disables the driving of the surgical saw blade 60 by a surgical saw blade driver illustrated in FIG. 5 for the reasons set forth above.

The pictorial representation of FIG. 12 is a combination of the saw blade driver 30 having a plurality of rectangular shaped driving lugs 36 terminating in a substantially rectangular outer end 38 arranged in a pattern as illustrated in FIG. 2 for enabling driving of a surgical saw blade 60 of the present invention. The generally rectangular elongated blade driving enabling section 88 of each slot 86 is configured for engaging with at least one of a plurality of rectangular driving lugs 36 terminating in a substantially rectangular outer end 38. The driving engagement enables the surgical saw blade to be responsive to the oscillatory driving motion of the rectangular shaped driving lugs 36 to drive the surgical saw blade.

The pictorial representation of FIG. 13 is a combination of the saw blade driver 40 having a plurality of rectangular shaped driving lugs 46 terminating in a substantially circular outer end 48 arranged in a pattern as illustrated in FIG. 3 for enabling driving of a surgical saw blade 60 of the present invention. The generally rectangular elongated blade driving enabling section 88 of each slot 86 is configured for engaging with at least one of a plurality of rectangular driving lugs 46 terminating in a substantially circular outer end 48. The driving engagement enables the surgical saw blade to be responsive to the oscillatory driving motion of the rectangular shaped driving lugs 46 to drive the surgical saw blade.

In the surgical saw blade of FIGS. 5 through 8, the plurality of slots 86 include a pair of driving slots positioned, shown by arrows 110, one on each side of the elongated slot 84 and centered relative to the hub center 84. The pair of slots 110 have an open end opposite the one end which terminates in an expanded bulbous blade driving disabling section 90.

In the surgical saw blade of FIGS. 5 through 8, the remainder of the plurality slots 86 have a closed end opposite the one end which terminates in an expanded bulbous blade driving disabling section 90.

In the surgical saw blade of FIGS. 5 through 8 which is the preferred embodiment of the present invention, the surgical saw blade 60 consists of seven slots, at least two of which, slots 110, have an open end opposite the one end which terminates in an expanded bulbous blade driving disabling section 90. The remaining at least five of the seven slots 86 have a closed end opposite the one end which terminates in an expanded bulbous blade driving disabling section 90.

As illustrated in FIGS. 5 through 8, the surgical saw blade 60 has a plurality of slots 86 having generally rectangular elongated blade driving enabling section 88 which are disposed in a pattern along a radius centered at the hub center 84 wherein the respective expanded bulbous blade driving disabling section 90 of each slot 86 is configured for disengaging from a plurality of driving circular pins 56 (shown in FIGS. 9, 10 and 11) arranged in a pattern of deflecting over a range of plus 5 degrees to minus 5 degrees.

The surgical saw blade 60 for penetrating bone is operatively coupled to an oscillatory power tool. the surgical saw blade has a distal end 72 and a proximal end 78 as discussed above. A cutting means is disposed at the distal end 72 of the surgical saw blade 60. A hub section 76 is disposed at the proximal end 78 for attachment to an oscillatory power tool for driving engagement with a hub section 76 having an outer periphery 76. The hub section 76 comprises an elongated slot 80 formed in the hub section 76 which extends from the outer periphery 76 along a longitudinal axis 66 to a U-shaped cut-out 82 forming a hub center 84. The hub center 84 is located along the longitudinal axis 66.

The hub section 76 includes a plurality of slots 86. Each of the slots 86 having a generally rectangular elongated blade driving enabling section 88 having one end which terminates in an expanded bulbous blade driving disabling section 90 in a position opposed to the hub center 84. The respective generally rectangular elongated blade driving enabling section 88 are disposed in a pattern along a radius centered at the hub center 84. The respective generally rectangular elongated blade driving enabling section 88 of each slot 86 is configured for engaging with at least one of a plurality of driving rectangular driving lugs terminating in a substantially rectangular outer end (such as shown in FIG. 12) arranged in a pattern and a plurality of rectangular driving lugs terminating in a substantially circular outer end (such as shown in FIG. 13) arranged in a pattern to drive the surgical saw blade 60 in response to a driving force therefrom. The respective expanded bulbous blade driving disabling section 90 of each slot 86 is configured for disengaging from a plurality of driving circular pins 56 (shown in FIGS. 9, 10 and 11) arranged in a pattern by deflecting a driving force therefrom along a locus of points which avoids driving the surgical saw blade in response to a driving force therefrom.

A surgical saw blade 60 for use in combination with a surgical bone saw is disclosed herein. The surgical saw blade comprises a distal end 72 having a plurality of teeth 70 for cutting bone. The hub section 74 has a proximal end 78 configured to couple to a surgical bone saw facilitates, such as shown in FIGS. 12 and 13. A hub section disposed at the proximal end 78 attachment or surgical saw blade to an oscillatory power tool for driving engagement with a hub section having an outer periphery. The hub section 74 comprises the structure illustrated in FIGS. 5 through 8.

Also, this invention relates to a combination of surgical bone saw and a bone saw blade. The surgical bone saw may be an oscillatory or sagittal bone saw. The surgical saw blade has a distal end 72 having teeth 70 for cutting bone. The proximal end of the surgical saw blade is configured to couple a surgical bone saw and has a hub section having an outer periphery. The structure of the surgical saw blade is illustrated in FIGS. 5 through 8.

A method of cutting bone comprising the steps of:

a) providing a surgical saw blade illustrated in FIGS. 5 through 8; coupling the surgical saw blade to a surgical saw; actuating the surgical saw with the coupled saw blade; and cutting the bone.

A method of cutting bone is shown. The method comprises the steps of providing a saw blade illustrated in FIGS. 5 through 8 having a hub section having an outer periphery located at one end of a saw blade body wherein the hub section comprises an elongated slot formed in the hub section which extends from the outer periphery along a longitudinal axis to a U-shaped cut-out forming a hub center, the hub center being along the longitudinal axis and wherein the hub section further comprises a plurality of slots, each of the slots having a generally rectangular elongated blade driving enabling section having one end which terminates in an expanded bulbous blade driving disabling section positioned opposed to the hub center, the respective generally rectangular elongated blade driving enabling section being disposed in a pattern along a radius centered at the hub center; coupling the saw blade to a surgical saw; actuating the surgical saw with the coupled saw blade; and cutting the bone.

It is envisioned that the surgical saw blade in substantially the preferred embodiment or a variation thereof may be fabricated to be driven by certain other saw blade drivers using the teachings herein of an enlarged bulbous blade driving disabling section. It will be appreciated that various alterations and modifications may be made to the surgical saw blade to enhance the functional features and/or characteristics thereof. All such variations and modifications should be considered to fall within the scope of the invention as broadly hereinbefore described and as claimed hereafter.

All such uses, variations, modifications and the like are anticipated to be within the scope of this invention.

What is claimed is:

1. A saw blade comprising
  a blade body having a longitudinal axis;
  a cutting means disposed at a first end of said blade body;
  a prearranged hub section having an outer periphery located at a second end of said blade body, said prearranged hub section comprising
    an elongated slot formed in said hub section which extends from said outer periphery along a longitudinal axis to a U-shaped cutout forming a hub center, said hub center being along said longitudinal axis;
    a plurality of slots, each of said slots having a generally rectangular elongated blade driving enabling section having one end which terminates in an expanded bulbous blade driving disabling section in a position opposed to the hub center, the respective generally rectangular elongated blade driving enabling section being disposed in a pattern along a radius centered at the hub center;
  said respective generally rectangular elongated blade driving enabling section of each slot being configured for engaging with at least one of a plurality of rectangular driving lugs terminating in a substantially rectangular outer end arranged in a pattern and a plurality of rectangular driving lugs terminating in a substantially circular outer end arranged in a pattern to drive said saw blade in response to a driving force therefrom and wherein said respective expanded bulbous blade driving disabling section of each slot is substantially oval shaped or substantially oval shaped having an indentation extending substantially perpendicular to the substantially oval shape and in a direction away from the hub center and dimensioned for disengaging from a plurality of circular driving pins arranged in a pattern disengaging over a predetermined range of a plus angle and a minus angle a driving force therefrom along a locus of points which avoids driving said saw blade in response to a driving force therefrom.

2. The saw blade of claim 1 wherein said plurality of slots include
  a pair of driving slots positioned one on each side of said elongated slot and centered relative to the hub center.

3. The saw blade of claim 2 wherein each of the pair of driving slots have an open end opposite said one end which terminates in an expanded bulbous blade driving disabling section.

4. The saw blade of claim 3 wherein the remainder of said plurality slots have a closed end opposite said one end which terminates in an expanded bulbous blade driving disabling section.

5. The saw blade of claim 1 consists of seven slots, at least two of which have an open end opposite said one end which terminates in an expanded bulbous blade driving disabling section.

6. The saw blade of claim 5 wherein at least five of the seven slots have a closed end opposite said one end which terminates in an expanded bulbous blade driving disabling section.

7. The saw blade of claim 1 wherein said plurality of slots generally rectangular elongated blade driving enabling section are disposed in a pattern along a radius centered at the hub center wherein said respective expanded bulbous blade driving disabling section of each slot are substantially oval shaped or substantially oval shaped having an indentation extending substantially perpendicular to the substantially oval shape and in a direction away from the hub center and dimensioned for disengaging from a plurality of circular driving pins arranged in a pattern of disengaging over a range of plus 5 degrees to minus 5 degrees the driving force from said plurality of circular driving pins arranged in a pattern.

8. A saw blade having a prearranged hub section having an outer periphery located at one end of a saw blade body, said hub section comprising
  an elongated slot formed in said hub section which extends from said outer periphery along a longitudinal axis to a U-shaped cut-out forming a hub center, said hub center being along said longitudinal axis; and
  a plurality of slots, each of said slots having a generally rectangular elongated blade driving enabling section having one end which terminates in an expanded bulbous blade driving disabling section in a position opposed to the hub center, the respective generally rectangular elongated blade driving enabling section being disposed in a pattern along a radius centered at the hub center and wherein said respective expanded bulbous blade driving disabling section of each slot are substantially oval shaped or substantially oval shaped having an indentation extending substantially perpendicular to the substantially oval shape and in a direction away from the hub center and dimensioned for disengaging from a plurality of circular driving pins arranged in a pattern by disengaging over a range of a plus 5 degrees and a minus 5 degrees a driving force therefrom along a locus of points which avoids driving said saw blade in response to a driving force therefrom.

9. A surgical saw blade for penetrating bone when said surgical saw blade is operatively coupled to an oscillatory power tool, comprising:
   a surgical saw blade having a distal end and a proximal end;
   a cutting means disposed at said distal end of said surgical saw blade;
   a hub disposed at said proximal end for attachment to an oscillatory power tool for driving engagement with a hub section having an outer periphery, said hub section comprising
      an elongated slot formed in said hub section which extends from said outer periphery along a longitudinal axis to a U-shaped cut-out forming a hub center, said hub center being along said longitudinal axis;
      a plurality of slots, each of said slots having a generally rectangular elongated blade driving enabling section having one end which terminates in an expanded bulbous blade driving disabling section in a position opposed to the hub center, the respective generally rectangular elongated blade driving enabling section being disposed in a pattern along a radius centered at the hub center;
   said respective generally rectangular elongated blade driving enabling section of each slot being configured for engaging with at least one of a plurality of rectangular driving lugs terminating in a substantially rectangular outer end arranged in a pattern and a plurality of rectangular driving lugs terminating in a substantially circular outer end arranged in a pattern to drive said saw blade in response to a driving force therefrom and wherein said respective expanded bulbous blade driving disabling section of each slot are substantially oval shaped or substantially oval shaped having an indentation extending substantially perpendicular to the substantially oval shape and in a direction away from the hub center and dimensioned for disengaging from a plurality of circular driving pins arranged in a pattern by disengaging over a range of a plus angle of 5 degree and a minus angle of 5 degree a driving force therefrom along a locus of points which avoids driving said saw blade in response to a driving force therefrom.

10. A surgical saw blade for use in combination with a surgical bone saw, the surgical saw blade comprising:
    a distal end having a plurality of teeth for cutting bone;
    a proximal end configured to couple to a surgical bone saw;
    a hub disposed at said proximal end for attachment to an oscillatory power tool for driving engagement with a hub section having an outer periphery, said hub section comprising
       an elongated slot formed in said hub section which extends from said outer periphery along a longitudinal axis to a U-shaped cutout forming a hub center, said hub center being along said longitudinal axis;
       a plurality of slots, each of said slots having a generally rectangular elongated blade driving enabling section having one end which terminates in an expanded bulbous blade driving disabling section in a position opposed to the hub center, the respective generally rectangular elongated blade driving enabling section being disposed in a pattern along a radius centered at the hub center and wherein said respective expanded bulbous blade driving disabling section of each slot are substantially oval shaped or substantially oval shaped having an indentation extending substantially perpendicular to the substantially oval shape and in a direction away from the hub center and dimensioned for disengaging from a plurality of circular driving pins arranged in a pattern by disengaging over a range of a plus angle of 5 degree and a minus angle of 5 degree a driving force therefrom along a locus of points which avoids driving said saw blade in response to a driving force therefrom.

11. The surgical saw blade of claim 10 wherein said respective generally rectangular elongated blade driving enabling section of each slot being configured for engaging with at least one of a plurality of rectangular driving lugs terminating in a substantially rectangular outer end arranged in a pattern and a plurality of rectangular driving lugs terminating in a substantially circular outer end arranged in a pattern to drive said saw blade in response to a driving force therefrom and wherein said respective expanded bulbous blade driving disabling section of each slot are substantially oval shaped or substantially oval shaped having an indentation extending substantially perpendicular to the substantially oval shape and in a direction away from the hub center and dimensioned for disengaging from a plurality of circular driving pins arranged in a pattern by disengaging a driving force therefrom along a locus of points which avoids driving said saw blade in response to a driving force therefrom.

12. In combination, a surgical bone saw and a bone saw blade comprising:
    an oscillatory or sagittal bone saw; and
    surgical saw blade having;
       a distal end having teeth for cutting bone; and
       a proximal end configured to couple to a surgical bone saw, said proximal end having a hub section having an outer periphery located at a second end of said blade body, said hub section comprising
          an elongated slot formed in said hub section which extends from said outer periphery along a longitudinal axis to a U-shaped cutout forming a hub center, said hub center being along said longitudinal axis;
          a plurality of slots, each of said slots having a generally rectangular elongated blade driving enabling section having one end which terminates in an expanded bulbous blade driving disabling section in a position opposed to the hub center, the respective generally rectangular elongated blade driving enabling section being disposed in a pattern along a radius centered at the hub center;
       said respective generally rectangular elongated blade driving enabling section of each slot being configured for engaging with at least one of a plurality of rectangular driving lugs terminating in a substantially rectangular outer end arranged in a pattern and a plurality of rectangular driving lugs terminating in a substantially circular outer end arranged in a pattern to drive said saw blade in response to a driving force therefrom and wherein said respective expanded bulbous blade driving disabling section of each slot are substantially oval shaped or substantially oval shaped having an indentation extending substantially perpendicular to the substantially oval shape and in a direction away from the hub center and dimensioned for disengaging from a plurality of circular driving pins arranged in a pattern by disengaging over a range of a plus angle of 5 degree and a minus angle of 5 degree a driving force therefrom along a locus of points which avoids driving said saw blade in response to a driving force therefrom.

13. A method of cutting bone comprising the steps of:
a) providing a surgical saw blade according to claim 1;
b) coupling the saw blade to a surgical saw;
c) actuating the surgical saw with the coupled saw blade; and
d) cutting the bone.

14. A method of cutting bone comprising the steps of providing a saw blade having a hub section having an outer periphery located at one end of a saw blade body wherein said said hub section comprises an elongated slot formed in said hub section which extends from said outer periphery along a longitudinal axis to a U-shaped cut-out forming a hub center, said hub center being along said longitudinal axis and wherein said hub section further comprises a plurality of slots, each of said slots having a generally rectangular elongated blade driving enabling section having one end which terminates in an expanded bulbous blade driving disabling section in a position opposed to the hub center, the respective generally rectangular elongated blade driving enabling section being disposed in a pattern along a radius centered at the hub center and wherein said respective expanded bulbous blade driving disabling section of each slot are substantially oval shaped or substantially oval shaped having an indentation extending substantially perpendicular to the substantially oval shape and in a direction away from the hub center and dimensioned for disengaging from a plurality of circular driving pins arranged in a pattern by disengaging over a range of a plus angle of 5 degree and a minus angle of 5 degree a driving force therefrom along a locus of points which avoids driving said saw blade in response to a driving force therefrom;
coupling the saw blade to a surgical saw;
actuating the surgical saw with the coupled saw blade; and
cutting the bone.

15. A surgical saw blade for penetrating bone when said surgical saw blade is operatively coupled to an oscillatory power tool, comprising:
a surgical saw blade having a proximal end and a distal end;
said proximal end having a prearranged hub section for attachment to an oscillatory power tool for driving engagement thereby, said proximal end having
an outer periphery located at a second end of said blade body, said prearranged hub section comprising
an elongated slot formed in said hub section which extends from said outer periphery along a longitudinal axis to a U-shaped cut-out forming a hub center, said hub center being along said longitudinal axis;
a plurality of slots, each of said slots having a generally rectangular elongated blade driving enabling section having one end which terminates in an expanded bulbous blade driving disabling section in a position opposed to the hub center, the respective generally rectangular elongated blade driving enabling section being disposed in a pattern along a radius centered at the hub center;
said respective generally rectangular elongated blade driving enabling section of each slot being configured for engaging with at least one of a plurality of rectangular driving lugs terminating in a substantially rectangular outer end arranged in a pattern and a plurality of rectangular driving lugs terminating in a substantially circular outer end arranged in a pattern to drive said saw blade in response to a driving force therefrom and wherein said respective expanded bulbous blade driving disabling section of each slot is configured for disengaging from a plurality of circular driving pins arranged in a pattern by deflecting a driving force therefrom along a locus of points which avoids driving said saw blade in response to a driving force therefrom and wherein said respective expanded bulbous blade driving disabling section of each slot are substantially oval shaped or substantially oval shaped having an indentation extending substantially perpendicular to the substantially oval shape and in a direction away from the hub center and dimensioned for disengaging from a plurality of circular driving pins arranged in a pattern by disengaging over a range of a plus angle of 5 degree and a minus angle of 5 degree a driving force therefrom along a locus of points which avoids driving said saw blade in response to a driving force therefrom; and
said distal end having a plurality of cutting teeth.

16. A surgical saw blade having a prearranged hub section, said prearranged hub section comprising
an outer periphery located at a second end of said blade body, said prearranged hub section comprising
an elongated slot formed in said hub section which extends from said outer periphery along a longitudinal axis to a U-shaped cut-out forming a hub center, said hub center being along said longitudinal axis; and
a plurality of slots, each of said slots having a generally rectangular elongated blade driving enabling section having one end which terminates in an expanded bulbous blade driving disabling section in a position opposed to the hub center, the respective generally rectangular elongated blade driving enabling section being disposed in a pattern along a radius centered at the hub center;
said respective generally rectangular elongated blade driving enabling section of each slot being configured for engaging with at least one of a plurality of rectangular driving lugs terminating in a substantially rectangular outer end arranged in a pattern and a plurality of rectangular driving lugs terminating in a substantially circular outer end arranged in a pattern to drive said saw blade in response to a driving force therefrom and wherein said respective expanded bulbous blade driving disabling section of each slot is substantially oval shaped or substantially oval shaped having an indentation extending substantially perpendicular to the substantially oval shape and in a direction away from the hub center and dimensioned for disengaging from a plurality of circular driving pins arranged in a pattern by disengaging over predetermine range of a plus angle and a minus angle a driving force therefrom along a locus of points which avoids driving said saw blade in response to a driving force therefrom.

* * * * *